United States Patent
Kollar et al.

(10) Patent No.: US 12,245,767 B2
(45) Date of Patent: Mar. 11, 2025

(54) HANDHELD ELECTROMECHANICAL SURGICAL SYSTEM

(71) Applicant: Covidien LP, Mansfield, MA (US)

(72) Inventors: Charles R. Kollar, West Hartford, CT (US); Alexander Hart, Tolland, CT (US); Haley Strassner, Hamden, CT (US); David E. Valentine, Hamden, CT (US); James Delbo, North Haven, CT (US); Jonathan M. Sandor, North Haven, CT (US)

(73) Assignee: Covidien LP, Mansfield, MA (US)

( * ) Notice: Subject to any disclaimer, the term of this patent is extended or adjusted under 35 U.S.C. 154(b) by 282 days.

(21) Appl. No.: 17/347,129

(22) Filed: Jun. 14, 2021

(65) Prior Publication Data

US 2022/0008078 A1 Jan. 13, 2022

Related U.S. Application Data

(60) Provisional application No. 63/051,026, filed on Jul. 13, 2020.

(51) Int. Cl.
*A61B 17/115* (2006.01)
*A61B 17/00* (2006.01)
*A61B 17/072* (2006.01)

(52) U.S. Cl.
CPC . *A61B 17/1155* (2013.01); *A61B 2017/00486* (2013.01); *A61B 2017/0053* (2013.01); *A61B 2017/07257* (2013.01); *A61B 2017/07285* (2013.01)

(58) Field of Classification Search
CPC ...... A61B 17/1155; A61B 2017/00486; A61B 2017/0053; A61B 2017/07257; A61B 2017/07285
See application file for complete search history.

(56) References Cited

U.S. PATENT DOCUMENTS

| | | |
|---|---|---|
| 5,383,880 A | 1/1995 | Hooven |
| 5,667,517 A | 9/1997 | Hooven |
| 5,810,811 A | 9/1998 | Yates et al. |
| 7,032,798 B2 | 4/2006 | Whitman et al. |

(Continued)

FOREIGN PATENT DOCUMENTS

| | | |
|---|---|---|
| EP | 0536882 A2 | 4/1993 |
| EP | 2027819 A1 | 2/2009 |

(Continued)

OTHER PUBLICATIONS

European Search Report dated Nov. 30, 2021, issued in corresponding EP Appln. No. 21185126, 7 pages.

*Primary Examiner* — Shaun L David
*Assistant Examiner* — Rachael L Geiger

(57) ABSTRACT

A surgical instrument includes an annular reload, and an anvil assembly configured to move relative to the annular reload between an open position and a preset closed position, in which the anvil assembly and the annular reload define a preset gap distance therebetween. A processor of the surgical instrument is configured to determine a difference between the preset gap distance and an actual gap distance gap distance between the anvil assembly and the annular reload, and adjust a staple stroke and a cutting stroke by the determined difference between the preset gap distance and the actual gap distance.

20 Claims, 6 Drawing Sheets

(56) References Cited

U.S. PATENT DOCUMENTS

| | | |
|---|---|---|
| 8,012,170 B2 | 9/2011 | Whitman et al. |
| 8,808,311 B2 | 8/2014 | Heinrich et al. |
| 10,278,698 B2 | 5/2019 | Racenet |
| 10,363,036 B2 | 7/2019 | Yates et al. |
| 2004/0153124 A1 | 8/2004 | Whitman |
| 2008/0251568 A1 | 10/2008 | Zemlok et al. |
| 2008/0272172 A1 | 11/2008 | Zemlok et al. |
| 2009/0012556 A1 | 1/2009 | Boudreaux et al. |
| 2009/0057369 A1 | 3/2009 | Smith et al. |
| 2009/0090763 A1 | 4/2009 | Zemlok et al. |
| 2009/0108048 A1 | 4/2009 | Zemlok et al. |
| 2009/0112271 A1 | 4/2009 | Moskowitz et al. |
| 2010/0133318 A1 | 6/2010 | Boudreaux |
| 2010/0270355 A1 | 10/2010 | Whitman et al. |
| 2011/0017801 A1 | 1/2011 | Zemlok et al. |
| 2011/0125138 A1 | 5/2011 | Malinouskas et al. |
| 2012/0211542 A1 | 8/2012 | Racenet |
| 2016/0066916 A1* | 3/2016 | Overmyer .............. H02H 3/207 227/176.1 |
| 2017/0311938 A1 | 11/2017 | Nicholas et al. |
| 2019/0099181 A1* | 4/2019 | Shelton, IV ....... A61B 17/0682 |
| 2019/0200996 A1* | 7/2019 | Shelton, IV ......... A61B 90/361 |
| 2019/0200998 A1 | 7/2019 | Shelton, IV et al. |
| 2019/0261991 A1* | 8/2019 | Beckman ............. A61B 17/068 |
| 2020/0281594 A1* | 9/2020 | Adams ............. A61B 17/07207 |
| 2020/0405311 A1* | 12/2020 | Shelton, IV ....... G06K 7/10366 |

FOREIGN PATENT DOCUMENTS

| | | |
|---|---|---|
| EP | 2245994 A1 | 11/2010 |
| EP | 3498191 A2 | 6/2019 |
| EP | 3795094 A1 | 3/2021 |

* cited by examiner

HANDHELD ELECTROMECHANICAL SURGICAL SYSTEM

CROSS-REFERENCE TO RELATED APPLICATION

This application claims the benefit of and priority to U.S. Provisional Patent Application No. 63/051,026, filed Jul. 13, 2020, the entire contents of which is incorporated by reference herein.

BACKGROUND

1. Technical Field

The present disclosure relates to surgical devices. More specifically, the present disclosure relates to handheld electromechanical surgical systems for performing surgical procedures.

2. Background of Related Art

One type of surgical device is a circular clamping, cutting and stapling device. Such a device may be employed in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis, and an annular knife is fired to core a portion of the clamped tissue portions. After the end-to-end anastomosis has been effected, the circular stapling apparatus is removed from the surgical site.

A number of surgical device manufacturers have developed product lines with proprietary powered drive systems for operating and/or manipulating the surgical device. In many instances the surgical devices include a powered handle assembly, which is reusable, and a disposable staple cartridge assembly, end effector or the like that is selectively connected to the powered handle assembly prior to use and then disconnected from the staple cartridge assembly or end effector following use in order to be disposed of or in some instances sterilized for re-use.

The use of powered electro and endomechanical surgical staplers, including intelligent battery power, has grown tremendously over the past few decades. Advanced technology and informatics within these intelligent battery-powered stapling devices provide the ability to gather clinical data and drive design improvements to ultimately improve patient outcomes. Accordingly, a need exists for improved powered electro and endomechanical surgical staplers that are capable of evaluating conditions that affect staple formation with the intention of building a more intelligent stapling algorithm.

SUMMARY

In accordance with an aspect of the disclosure, a surgical instrument is provided and includes a handle assembly, an adapter assembly configured to selectively couple to the handle assembly, and an end effector. The handle assembly includes a memory having instructions stored therein, and a processor configured to execute the instructions. The adapter assembly includes a trocar and the end effector includes an anvil assembly configured to be coupled to the trocar, and an annular reload configured to selectively couple to a distal portion of the adapter assembly. The anvil assembly is configured to be moved relative to the annular reload between an open position and a preset closed position, in which the anvil assembly and the annular reload define a preset gap distance therebetween. The processor, using the instructions stored in the memory, is configured to determine a difference between the preset gap distance and an actual gap distance gap distance between the anvil assembly and the annular reload. The processor is further configured to adjust a staple stroke and a cutting stroke by the determined difference between the preset gap distance and the actual gap distance.

In aspects, the annular reload may include a plurality of staples and the staple stroke may be a linear distance traveled by the staples during ejection of the staples from the annular reload.

The annular reload may further include an annular knife and the cutting stroke may be a linear distance traveled by the annular knife during a cutting sequence of the annular knife.

In aspects, the memory may have stored therein a preset staple stroke and a preset cutting stroke each corresponding to the preset gap distance. The adjusted staple stroke may be the preset staple stroke minus the determined difference between the preset gap distance and the actual gap distance, and the adjusted cutting stroke may be the preset cutting stroke minus the difference between the preset gap distance and the actual gap distance.

In aspects, the processor may be further configured to determine whether the actual gap distance is less than the preset gap distance.

In aspects, the processor may be further configured to determine, when the end effector is in the closed position, whether a force exerted on the trocar is less than a threshold force. The processor may be further configured to retract the anvil assembly toward the annular reload in response to determining that the force exerted on the trocar is less than the threshold force.

In aspects, the processor may be further configured to set the gap distance upon determining that the force exerted on the trocar is at the threshold force.

In accordance with another aspect of the disclosure, a method of using a surgical instrument is provided and includes retracting an anvil assembly toward an annular reload from an open position to a closed position, in which a gap distance defined between the anvil assembly and the annular reload is at a preset gap distance; further retracting the anvil assembly toward the annular reload from the preset gap distance to an adjusted gap distance; and adjusting a staple stroke and a cutting stroke by a difference between the preset gap distance and the adjusted gap distance.

In aspects, the staple stroke may be a linear distance traveled by staples during ejection of the staples from the annular reload, and the cutting stroke may be a linear distance traveled by an annular knife during a cutting sequence of the annular knife.

In aspects, the adjusted staple stroke may be equal to a preset staple stroke minus the difference between the preset gap distance and the adjusted gap distance, and the adjusted cutting stroke may be equal to a preset cutting stroke minus the difference between the preset gap distance and the adjusted gap distance.

In aspects, the method may further include ejecting the staples from the annular reload by the adjusted staple stroke; and advancing the annular knife from the annular reload by the adjusted cutting stroke.

In aspects, the method may further include determining, when the anvil assembly is in the closed position, whether a force exerted on the anvil assembly by tissue is less than a threshold force. The anvil assembly may be further retracted in response to determining that the force exerted on the trocar is less than the threshold force.

In aspects, the method may further include setting the gap distance upon determining that the force exerted on the anvil assembly is at the threshold force.

In another aspect of the disclosure, a surgical instrument is provided and includes an adapter assembly including a trocar, an end effector and a handle assembly configured to couple to the adapter assembly. The end effector includes an annular reload configured to selectively couple to a distal portion of the adapter assembly and an anvil assembly. The annular reload includes a plurality of staples and an annular knife. The anvil assembly is configured to be coupled to the trocar and moved relative to the annular reload between an open position and a preset closed position, in which the anvil assembly and the annular reload define a preset gap distance therebetween. The handle assembly includes a processor configured to: determine a difference between the preset gap distance and an actual gap distance between the anvil assembly and the annular reload; and adjust a staple stroke and a cutting stroke by the determined difference between the preset gap distance and the actual gap distance.

In aspects, the handle assembly may include a memory storing a preset staple stroke and a preset cutting stroke each corresponding to the preset gap distance, In aspects, the adjusted staple stroke may be the preset staple stroke minus the determined difference between the preset gap distance and the actual gap distance. The adjusted cutting stroke may be the preset cutting stroke minus the difference between the preset gap distance and the actual gap distance.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
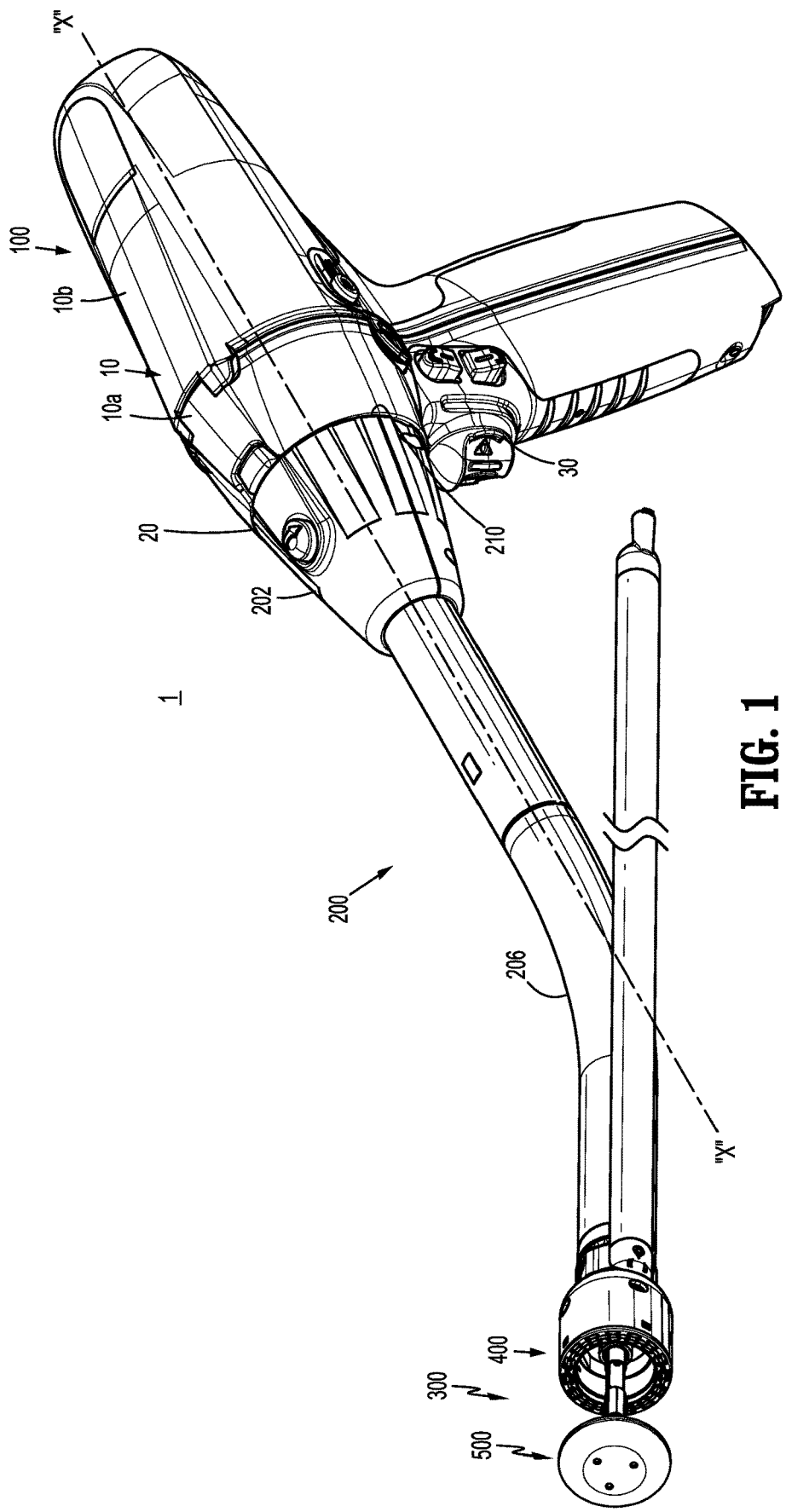
FIG. 1 is a perspective view of a handheld surgical instrument including a handle assembly, an adapter assembly, and an end effector, in accordance with an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

An intelligent surgical instrument, such as a hand-held surgical instrument, includes a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation. For example, in a case where extremely thin tissue is being treated, it may be advantageous to move an anvil of the end effector closer to a distal end of the adapter assembly in order to confirm that an anvil is attached to the adapter assembly.

This disclosure relates to software that will allow and compensate for anvil movement in situations when the stapler is already fully clamped and there is less than a target threshold load on the anvil. In this case, the stapler may move the anvil toward the adapter assembly (e.g., proximally) until the target threshold load is detected. To account for this, the staple stroke and cut stroke are adjusted to the corresponding delta anvil position. This maintains a consistent firing, regardless of clamp distance. The adjusted staple stroke maintains a consistent staple crimp even with the anvil out of position; and the adjusted cut stroke ensures a correct cut distance regardless of the anvil position.

FIG. 1 illustrates a surgical instrument, such as, for example, a circular stapler 1, including a handle assembly 100, which is configured for selective connection with an adapter assembly 200, and, in turn, adapter assembly 200 is configured for selective connection with an end effector 300, which includes a reload 400 (of a plurality of reloads) and an anvil assembly 500. The end effector 300 is configured to produce a surgical effect on tissue of a patient. The handle assembly 100 is a powered electromechanical handle assembly including a power handle 101 (FIG. 2) and an outer shell housing 10 configured to selectively receive and encase power handle 101. Outer shell housing 10 includes a distal half-section 10a and a proximal half-section 10b pivotably connected to distal half-section 10a. When joined, distal and proximal half-sections 10a, 10b define a shell cavity therein in which power handle 101 is selectively situated.

Distal and proximal half-sections 10a, 10b of shell housing 10 are divided along a plane that traverses a longitudinal axis "X" of adapter assembly 200. Distal half-section 10a of shell housing 10 defines a connecting portion 20 configured to accept a corresponding drive coupling assembly 210 (FIG. 3) of adapter assembly 200. Distal half-section 10a of shell housing 10 supports a distal facing toggle control button 30. Toggle control button 30 is capable of being actuated in a left, right, up and down direction upon application of a corresponding force thereto or a depressive force thereto.

Figure 2:
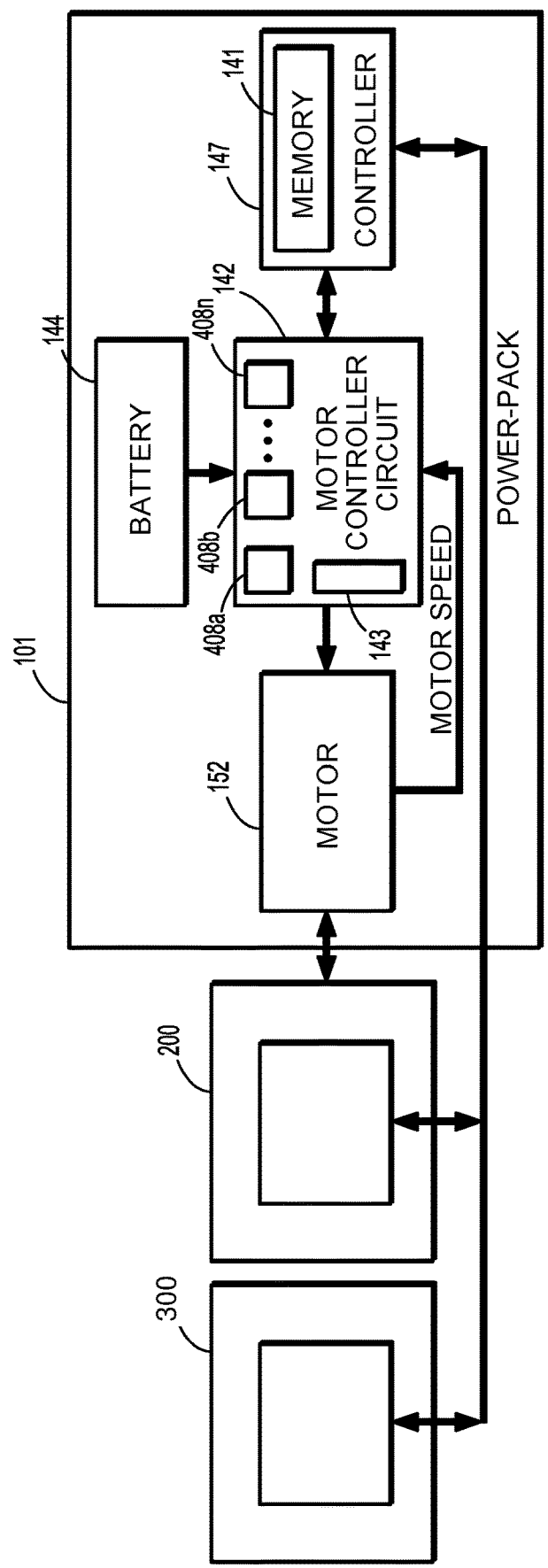
FIG. 2 is a schematic diagram of the handle assembly, the adapter assembly, and the end effector of FIG. 1.

With reference to FIGS. 1 and 2, the power handle 101 includes a controller circuit board 142, a rechargeable battery 144 configured to supply power to any of the electrical components of handle assembly 100, and a motor 152 coupled to the battery 144. In embodiments, the motor 152 may be coupled to any suitable power source configured to provide electrical energy to the motor 152, such as an AC/DC transformer. The battery 144 and the motor 152 are coupled to the motor controller circuit board 142 having a motor controller 143 which controls the operation of the motor 152 including the flow of electrical energy from the battery 144 to the motor 152. A main controller 147 is provided that controls the power handle 101.

The motor controller 143 includes a plurality of sensors 408a, 408b, . . . 408n configured to measure operational states of the motor 152 and the battery 144. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft (not shown) coupled thereto and rotatable by the motor 152. The position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the circular adapter assembly 200 and/or the end effector 300 by counting revolutions of the motor 152.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to a strain gauge (not explicitly shown) of the circular adapter assembly 200 using a wired or a wireless connection and is configured to receive strain measurements from the strain gauge which are used during operation of the power handle 101.

In addition to the first motor 152, the power handle 101 further includes a second motor (not explicitly shown) and a third motor (not explicitly shown) each electrically connected to controller circuit board 142 and battery 144. Each motor 152 includes a respective motor shaft (not explicitly shown) extending therefrom. Rotation of the motor shafts by the respective motors 152 function to drive shafts and/or gear components of adapter assembly 200 in order to perform the various operations of handle assembly 100. In particular, motors 152 of power handle 101 are configured to drive shafts and/or gear components of adapter assembly 200 in order to selectively extend/retract a trocar member 274 (FIG. 4) of a trocar assembly 270 of adapter assembly 200; to, open/close end effector 300 (when anvil assembly 500 is connected to trocar member 274 of trocar assembly 270), to fire an annular array of staples of reload 400, and to fire an annular knife (not explicitly shown) of reload 400.

Figure 3:
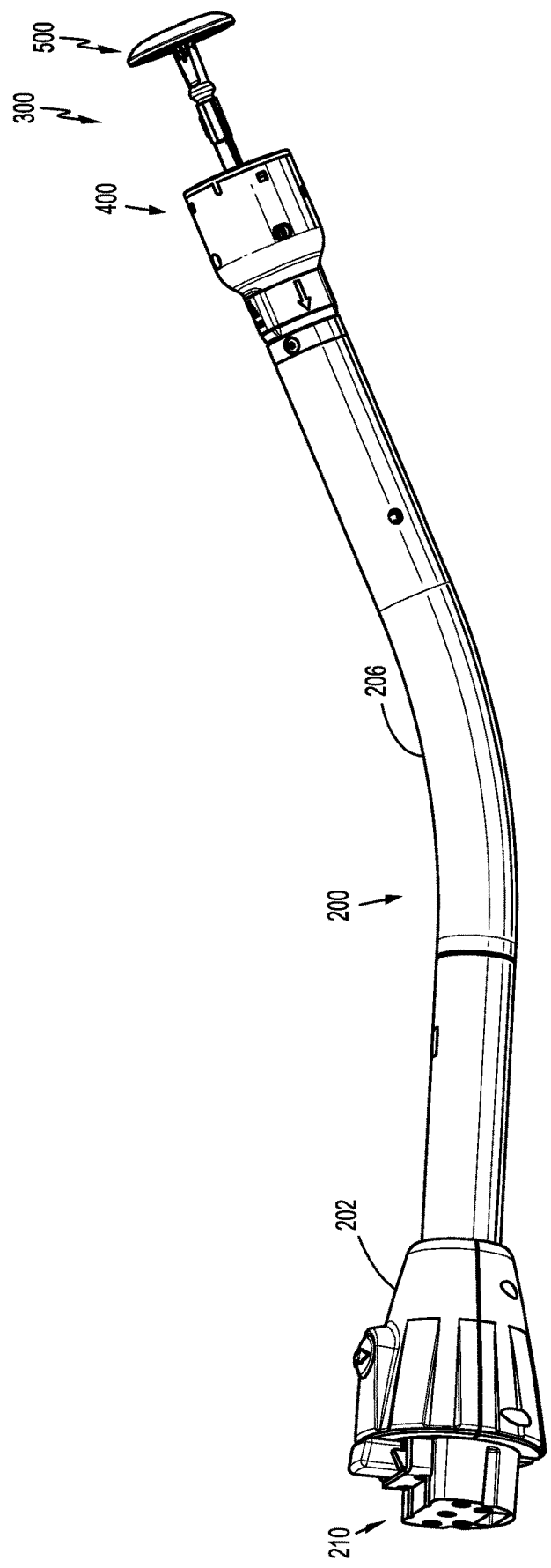
FIG. 3 is a side perspective view of the adapter assembly and the end effector (e.g., an annular reload and an anvil assembly) attached to the adapter assembly.
Figure 4:
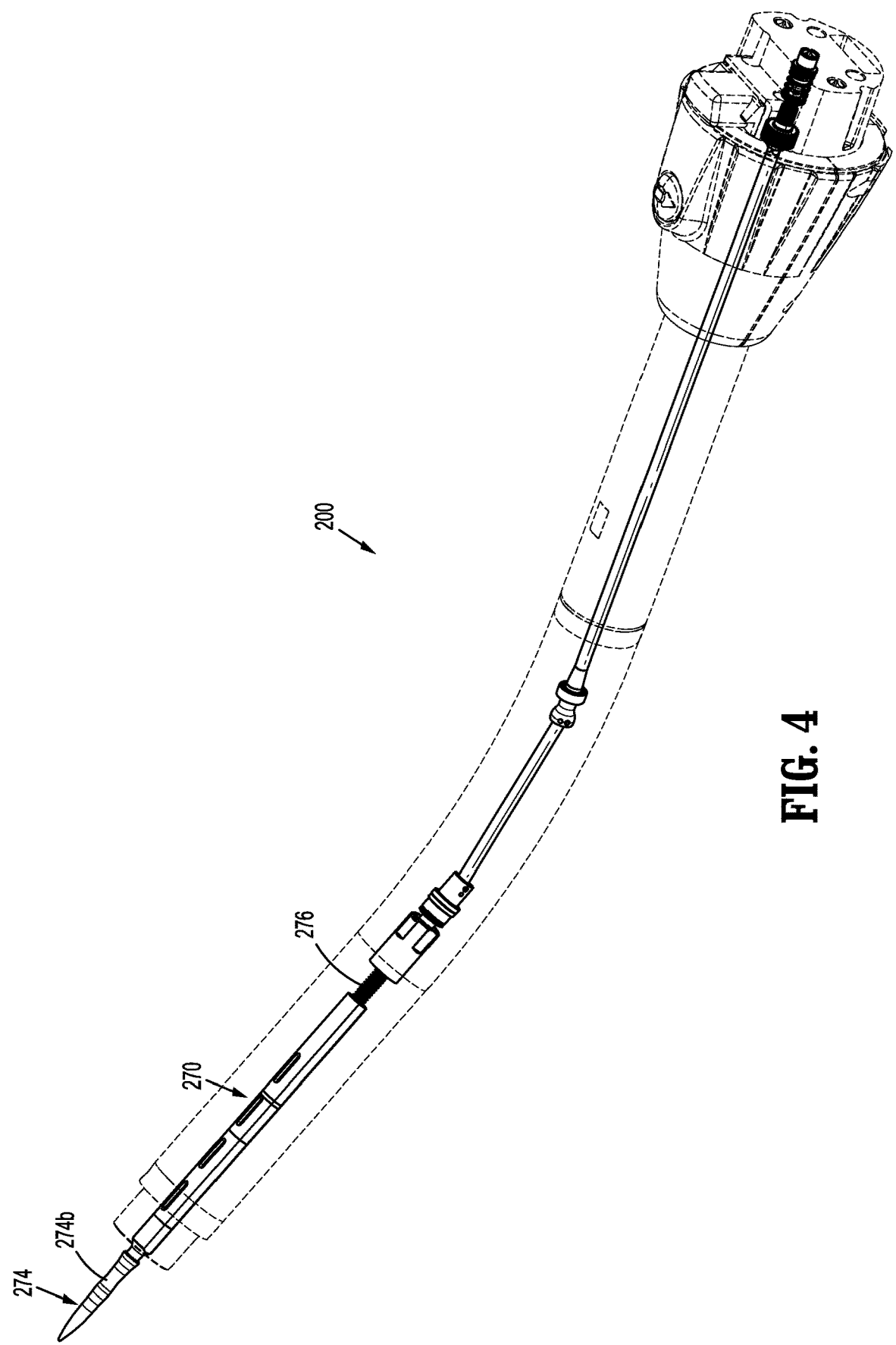
FIG. 4 is a perspective view of the adapter assembly, shown partially in phantom, without the end effector (e.g., the annular reload and the anvil assembly)

Turning now to FIGS. 3-4, adapter assembly 200 includes an outer knob housing 202 and an outer tube 206 extending from a distal end of knob housing 202. Knob housing 202 and outer tube 206 are configured and dimensioned to house the components of adapter assembly 200. Adapter assembly 200 is configured to convert a rotation of coupling shafts (not explicitly shown) of handle assembly 100 into axial translations useful for operating trocar assembly 270 of adapter assembly 200, anvil assembly 500, and/or staple driver assembly (not explicitly shown) or knife assembly (not explicitly shown) of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274b of trocar member 274 is configured to selectively engage anvil assembly 500, such that axial movement of trocar member 274, via a rotation of drive screw 276, results in a concomitant axial movement of anvil assembly 500.

Forces during an actuation of trocar member 274 or a closing of end effector 300 (e.g., a retraction of anvil assembly 500 relative to reload 400) may be measured by the strain gauge in order to monitor and control a firing of staples from reload 400; monitor forces during a firing and formation of the staples as the staples are being ejected from reload 400; optimize formation of the staples (e.g., staple crimp height) as the staples are being ejected from reload 400 for different indications of tissue; and monitor and control a firing of the annular knife of reload 400.

The strain gauge of adapter assembly 200 measures and monitors the retraction of trocar member 274. During the closing of end effector 300, if and when anvil assembly 500 contacts tissue, an obstruction, a tissue-contacting surface of annular reload 400, or the like, a reaction force is exerted on anvil assembly 500 which is in a generally distal direction. This distally directed reaction force is communicated from anvil assembly 500 to the strain gauge. The strain gauge then communicates signals to main controller circuit board 142 of power handle 101 of handle assembly 100. Graphics are then displayed on a display screen (not shown) of handle assembly 100 to provide the user with real-time information related to the status of the firing of handle assembly 100.

For further details regarding the construction and operation of the circular stapler and its components, reference may be made to International Application No. PCT/US2019/040440, filed on Jul. 3, 2019, the entire contents of which being incorporated by reference herein.

In operation, the anvil assembly 500 (already positioned by surgeon) is attached to the trocar member 274 and the user begins the clamping process on the tissue interposed between circular reload 400 and the anvil assembly 500 by pressing on the bottom of the toggle control button 30. During clamping, the anvil assembly 500 is retracted toward the circular reload 400 until reaching a preset, fully clamped position, namely a position of the anvil assembly 500 at which the tissue is fully clamped between the anvil assembly 500 and the reload 400. The preset, fully clamped position varies for each of the different types of reloads (e.g., the distance is about 29 mm for 25 mm reloads). While clamping, the strain gauge continuously provides measurements to the main controller 147 on the force imparted on the trocar member 274 as it moves the anvil assembly 500 to compress tissue between the anvil assembly 500 and the annular reload 400.

Upon reaching the fully clamped position (e.g., a preset gap distance defined between the anvil assembly 500 and the annular reload 400), the main controller 147 determines, using the measurements taken by the strain gauge, whether the measured force is at or less than a target threshold load. If the main controller 147 determines that the measured force is less than the target threshold load, this is an indication that the clamped tissue is extremely thin, and will therefore require that the gap distance between the anvil assembly 500 and the reload 400 be reduced to below the preset gap distance of the fully clamped position. As such, the anvil assembly 500 is further retracted beyond the fully clamped position until the target threshold load is detected, in which the anvil assembly 500 is in an over-clamped state. Since the gap distance between the anvil assembly 500 and the reload 400 is less than the preprogrammed gap distance for the end effector 300, the total amount of distal movement of the staples and the annular knife (e.g., the staple stroke and the cut stroke, respectively) during the respective stapling and cutting sequences should also be adjusted.

Figure 5A:
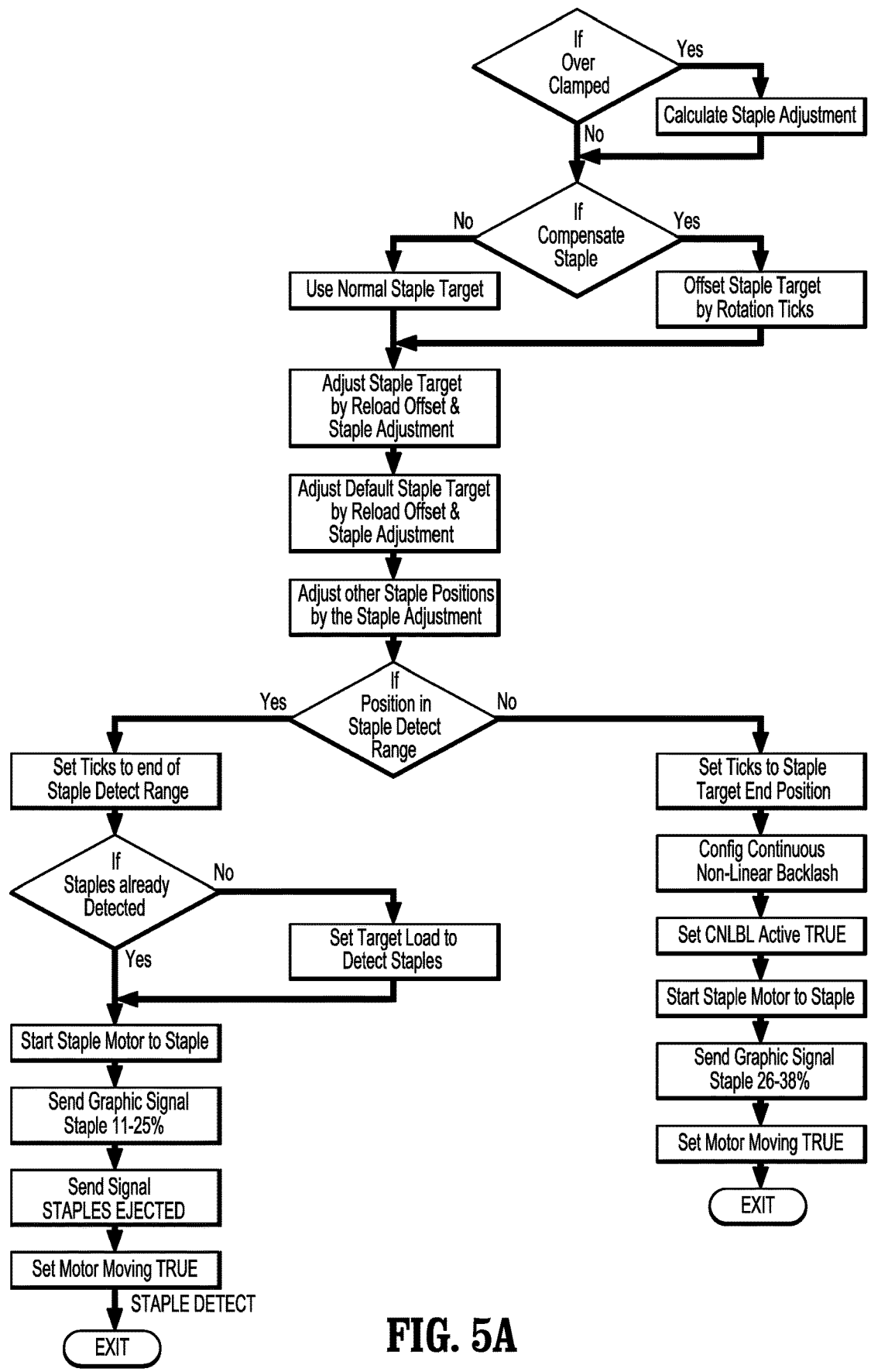
FIG. 5A is a flow chart of a method for carrying out a stapling function of the surgical instrument of FIG. 1.

With reference to FIG. 5A, which shows a flow chart of the stapling process, software stored in the memory 141 instructs the main controller 147 to determine whether the anvil assembly 500 is in the over-clamped state noted above. If the main controller 147 determines that the anvil assembly 500 has been retracted to the over-clamped state (e.g., due to the tissue having a thickness that is less than the pre-programmed gap distance), the main controller 147 calculates a staple adjustment. Staple adjustment may include decreasing the distance of the staple stroke compared with a preset staple stroke. The preset staple stroke may be adjusted (e.g., reduced) by the difference between the gap distance in the over-clamped state and the gap distance in the fully clamped state.

To commence the stapling sequence, the user presses down on the toggle control button 30, which results in ejection of the staples from the reload 400 into the anvil assembly 500 to deform the staples through the tissue. The staples are ejected from the reload 400 by the adjusted staple stroke to staple tissue. The main controller 147 determines that the stapling process is completed successfully if the measured strain was within minimum and maximum stapling force limits. Progress of staple firing is illustrated by an animation of the anastomosis, a firing progress bar, and staple formation.

Figure 5B:
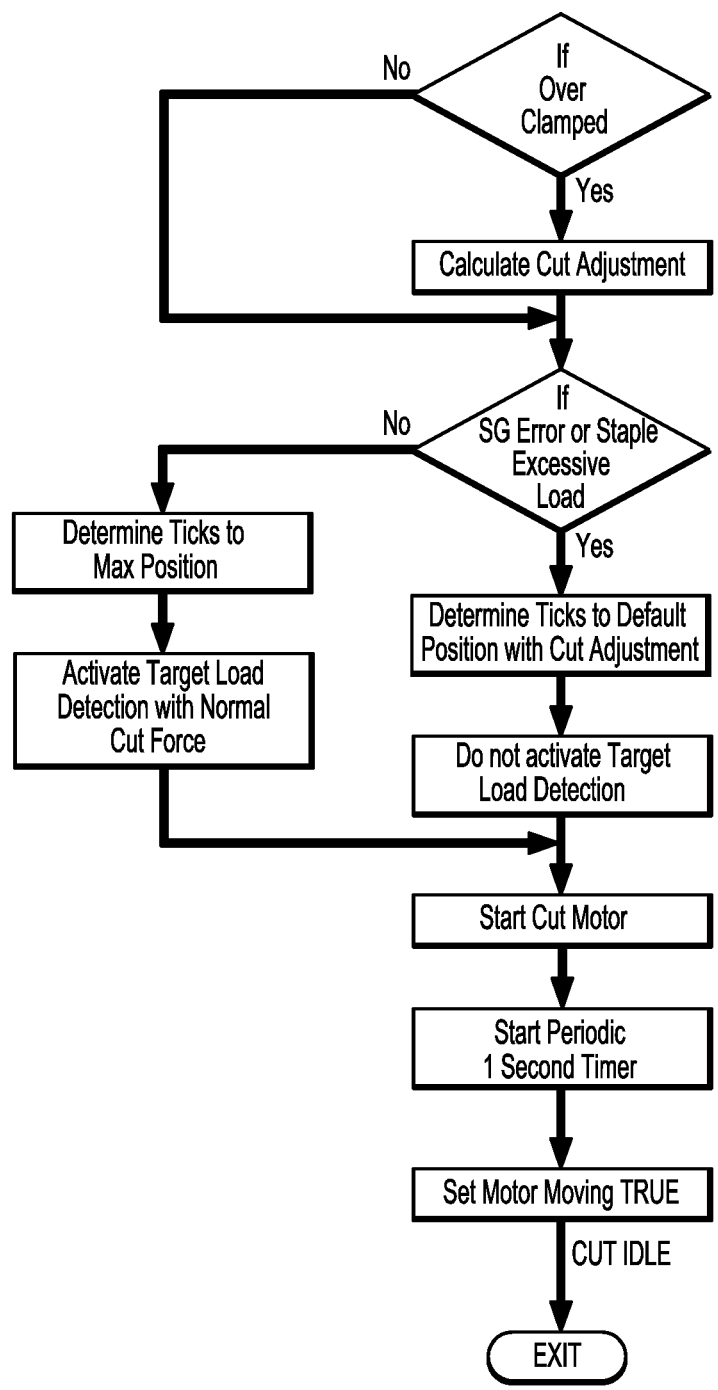
FIG. 5B is a flow chart of a method for carrying out a cutting function of the surgical instrument of FIG. 1.

With reference to FIG. 5B, which shows a flow chart of the cutting process, the software stored in the memory 141 includes instructions that when executed by the main controller 147 allows the main controller 147 to determine whether the anvil assembly 500 is in the over-clamped state. If the main controller 147 determines that the anvil assembly 510 has been approximated to the over-clamped state (e.g., due to the tissue having a thickness that is less than the pre-programmed gap distance), the main controller 147 calculates a cutting adjustment, such as, for example, a decrease in cutting stroke compared with a preset cutting stroke. The preset cutting stroke is adjusted (e.g., reduced) by the difference between the gap distance in the over-clamped state and the gap distance in the fully clamped state. As such, upon actuating the cutting function, the knife is translated from the reload 400 by the adjusted cutting stroke.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical instrument comprising:
 a handle assembly including a memory having instructions stored therein, and a processor configured to execute the instructions;
 an adapter assembly configured to selectively couple to the handle assembly, the adapter assembly including a trocar; and
 an end effector including:
  an annular reload configured to selectively couple to a distal portion of the adapter assembly and configured for a stapling sequence and a cutting sequence; and
  an anvil assembly configured to be coupled to the trocar and moved relative to the annular reload between an open position and a preset closed position, wherein the anvil assembly and the annular reload define a preset gap distance therebetween when in the preset closed position;
 wherein the processor, using the instructions stored in the memory, is configured to:
  determine a difference between the preset gap distance and an actual gap distance between the anvil assembly and the annular reload when the anvil assembly is in an actual closed position; and
  prior to the stapling sequence and the cutting sequence, adjust each of a staple stroke for the stapling sequence and a cutting stroke for the cutting sequence by the determined difference between the preset gap distance and the actual gap distance.

2. The surgical instrument according to claim 1, wherein the annular reload includes one or more staples and the staple stroke is a linear distance traveled by the one or more staples during the stapling sequence.

3. The surgical instrument according to claim 2, wherein the annular reload further includes an annular knife and the cutting stroke is a linear distance traveled by the annular knife during the cutting sequence.

4. The surgical instrument according to claim 3, wherein the memory has stored therein a preset staple stroke and a preset cutting stroke each corresponding to the preset gap distance, and wherein the adjusted staple stroke is the preset staple stroke minus the determined difference between the preset gap distance and the actual gap distance, and the adjusted cutting stroke is the preset cutting stroke minus the difference between the preset gap distance and the actual gap distance.

5. The surgical instrument according to claim 1, wherein the processor is further configured to determine whether the actual gap distance is less than the preset gap distance.

6. The surgical instrument according to claim 1, wherein the processor is further configured to:
   determine, when the end effector is in the preset closed position, that a force exerted on the trocar is less than a threshold force; and
   retract the anvil assembly toward the annular reload to the actual closed position in response to determining that the force exerted on the trocar is less than the threshold force.

7. The surgical instrument according to claim 6, wherein the processor is further configured to update the preset gap distance upon determining that the force exerted on the trocar is at the threshold force.

8. A method of using a surgical instrument, the method comprising:
   retracting an anvil assembly toward an annular reload from an open position to a preset closed position, with the anvil assembly and the annular reload defining a preset gap distance when in the preset closed position, wherein the annular reload is configured for a stapling sequence and a cutting sequence;
   further retracting the anvil assembly toward the annular reload from the preset closed position to an actual closed position defining an actual gap distance for further tissue compression;
   determining a difference between the preset gap distance and the actual gap distance between the anvil assembly and the annular reload; and
   prior to the stapling sequence and the cutting sequence, adjusting each of a staple stroke of the stapling sequence and a cutting stroke of the cutting sequence by the determined difference between the preset gap distance and the actual gap distance.

9. The method according to claim 8, wherein the staple stroke is a linear distance traveled by one or more staples during the stapling sequence, and the cutting stroke is a linear distance traveled by an annular knife during the cutting sequence.

10. The method according to claim 9, wherein the surgical instrument comprises a memory storing a preset staple stroke and a preset cutting stroke, and wherein the adjusted staple stroke is equal to the preset staple stroke minus the difference between the preset gap distance and the actual gap distance, and wherein the adjusted cutting stroke is equal to the preset cutting stroke minus the difference between the preset gap distance and the actual gap distance.

11. The method according to claim 10, further comprising:
   ejecting the one or more staples from the annular reload by the adjusted staple stroke; and
   advancing the annular knife from the annular reload by the adjusted cutting stroke.

12. The method according to claim 8, further comprising determining, when the anvil assembly is in the preset closed position, that a force exerted on the anvil assembly by tissue is less than a threshold force, wherein the anvil assembly is further retracted to the actual closed position in response to determining that the force exerted on the anvil assembly is less than the threshold force.

13. The method according to claim 12, further comprising updating the preset gap distance upon determining that the force exerted on the anvil assembly is at the threshold force.

14. A surgical instrument comprising:
   an adapter assembly including a trocar;
   an end effector including:
      an annular reload configured to selectively couple to a distal portion of the adapter assembly and having one or more staples and an annular knife, the annular reload configured for a stapling sequence and a cutting sequence; and
      an anvil assembly configured to be coupled to the trocar and moved relative to the annular reload between an open position and a preset closed position, wherein the anvil assembly and the annular reload define a preset gap distance therebetween when in the preset closed position;
   a force sensor configured to sense an applied force on the trocar while moving the anvil assembly; and
   a processor operably coupled to the adapter assembly and communicatively coupled to the force sensor, and configured to:
      retract the anvil assembly toward the annular reload until the applied force on the trocar reaches a target threshold load to define an actual gap distance;
      determine a difference between the preset gap distance and the actual gap distance between the anvil assembly and the annular reload; and
      prior to the stapling sequence and the cutting sequence, adjust each of a staple stroke and a cutting stroke by the determined difference between the preset gap distance and the actual gap distance.

15. The surgical instrument according to claim 14, wherein the staple stroke is a linear distance traveled by one or more staples during the stapling sequence, and the cutting stroke is a linear distance traveled by an annular knife during the cutting sequence.

16. The surgical instrument according to claim 15, further comprising a memory storing a preset staple stroke and a preset cutting stroke each corresponding to the preset gap distance.

17. The surgical instrument according to claim 16, wherein the adjusted staple stroke is the preset staple stroke minus the determined difference between the preset gap distance and the actual gap distance, and the adjusted cutting stroke is the preset cutting stroke minus the difference between the preset gap distance and the actual gap distance.

18. The surgical instrument according to claim 14, wherein the processor is further configured to determine whether the actual gap distance is less than the preset gap distance.

19. The surgical instrument according to claim 14, wherein the processor is further configured to:
   determine, when the end effector is in the preset closed position, a that the applied force exerted on the trocar is less than the target threshold load; and
   further retract the anvil assembly toward the annular reload in response to determining that the force exerted on the trocar is less than the target threshold load.

20. The surgical instrument according to claim 19, wherein the processor is further configured to update the preset gap distance upon determining that the applied force exerted on the trocar is at the target threshold load.

* * * * *